(12) United States Patent
Schörken et al.

(10) Patent No.: US 7,799,544 B2
(45) Date of Patent: Sep. 21, 2010

(54) COMPOSITIONS WHICH CAN BE USED AS BIOFUEL

(75) Inventors: Ulrich Schörken, Düsseldorf (DE); Carolin Meyer, Düsseldorf (DE); Matthias Hof, Duisburg (DE); Nigel Cooban, Merseyside (GB); Diana Stuhlmann, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 581 days.

(21) Appl. No.: 11/795,667

(22) PCT Filed: Jan. 10, 2006

(86) PCT No.: PCT/EP2006/000121

§ 371 (c)(1),
(2), (4) Date: Jul. 19, 2007

(87) PCT Pub. No.: WO2006/077023

PCT Pub. Date: Jul. 27, 2006

(65) Prior Publication Data

US 2008/0153143 A1 Jun. 26, 2008

(30) Foreign Application Priority Data

Jan. 19, 2005 (DE) ........................ 10 2005 002 700

(51) Int. Cl.
*C12P 7/64* (2006.01)
*C10L 1/18* (2006.01)

(52) U.S. Cl. ......................................... 435/134; 44/388

(58) Field of Classification Search ........................ None
See application file for complete search history.

(56) References Cited

U.S. PATENT DOCUMENTS

| | | | |
|---|---|---|---|
| 4,695,411 A * | 9/1987 | Stern et al. | ................... 554/167 |
| 5,116,745 A | 5/1992 | Mazur et al. | |
| 5,316,927 A | 5/1994 | Zaks et al. | |
| 5,935,828 A | 8/1999 | Zaks et al. | |
| 5,968,792 A | 10/1999 | Wenzel et al. | |
| 6,013,817 A | 1/2000 | Stern et al. | |
| 6,605,452 B1 | 8/2003 | Basheer | |
| 6,905,850 B2 | 6/2005 | Irimescu et al. | |
| 2004/0034244 A1 | 2/2004 | Bournay et al. | |
| 2005/0113588 A1 | 5/2005 | Hillion et al. | |
| 2006/0288636 A1 | 12/2006 | Iijima et al. | |

FOREIGN PATENT DOCUMENTS

| | | |
|---|---|---|
| EP | 0 198 243 A2 | 10/1986 |
| EP | 0 407 959 A2 | 1/1991 |
| EP | 1 460 124 A1 | 9/2004 |
| FR | 2 772 391 A1 | 6/1999 |
| JP | 3-103499 A | 4/1991 |
| JP | 3-108489 A | 5/1991 |
| JP | 3-187385 A | 8/1991 |
| WO | WO 90/04033 A1 | 4/1990 |
| WO | WO 90/13656 A1 | 11/1990 |
| WO | WO 91/16441 A1 | 10/1991 |
| WO | WO 91/16442 A1 | 10/1991 |
| WO | WO 95/03377 | 2/1995 |
| WO | WO 00/63322 A1 | 10/2000 |
| WO | WO 01/19941 A1 | 3/2001 |
| WO | WO 02/06505 A1 | 1/2002 |
| WO | WO 2004/052874 A1 | 6/2004 |
| WO | WO 2005/017075 A1 | 2/2005 |

OTHER PUBLICATIONS

Omar I C et al: "Purification and Some Properties of a Thermostable Lipase From Humicola-Lanuginosa No. 3" Agricultural and Biological Chemistry, vol. 51, No. 1, 1987, pp. 37-46, XP009087321.
Kaieda Masaru et al: "Effect of methanol and water contents on production of biodiesel fuel from plant oil catalyzed by various lipases in a solvent-free system" Journal of Bioscience and Bioengineering, vol. 9, No. 1, Jan. 9, 2001, pp. 12-15, XP002444785.
Fukuda H et al: "Biodiesel fue production by transesterification of oils" Journal of Bioscience and Bioengineering, Elsevier, Amsterdam, NL, vol. 92, No. 5, 2001, pp. 405-416, XP002983530.
Noureddini H et al: "Immobilized Pseudomonas cepacia lipase for biodiesel fuel production from soybean oil" Bioresource Technology, Elsevier, GB, vol. 96, No. 7, May 2005, pp. 769-777, XP004679790.
Soumanou M M et al: "Lipase-Catalyzed Alcoholysis of Vegetable Oils" European Journal of Lipid Science and Technology, Wiley VCH Verlag, Weinheim, DE, vol. 105, No. 11, Oct. 2003, pp. 656-660, XP001178392.
Soumanou Mohamed M et al: "Improvement in lipase-catalyzed synthesis of fatty acid methyl esters from sunflower oil", Enzyme and Microbial Technology, vol. 33, No. 1, Jul. 16, 2003, pp. 97-103, XP002444784.
Du Wei et al: "Novozyrn 435-catalyzed transesterification of crude soya bean oils for biodiesel production in a solvent-free medium" Biotechnology and Applied Biochemistry, vol. 40, No. Part 2, Oct. 2004, pp. 187-190, XP009087304.
Hua-Lin Wu et al: "Immobilization of Proteins by Reductive Alkylation with Hydrophobic Aldehydes", Biotechnology and Bioengineering, Wiley & Sons, Hoboken, NJ, US, vol. 23, No. 4, Apr. 1981, pp. 855-861, XP002412297.
Bornscheuer, "Recent advances in the lipase-catalyzed biotransformation of fats and oils", Recent Res. Devel. Oil Chem., 3, (1999), pp. 93-106.
Hydrolases in Organic Synthesis, Wiley-VCH, 1999, eds. Bornscheuer & Kazlaukas (book).

* cited by examiner

*Primary Examiner*—Herbert J. Lilling

(57) ABSTRACT

A composition comprising alkyl esters, with a $C_1$-$C_8$ alkyl group, and partial glycerides, with a free glycerol content of, at most, 2%, by weight, based on the weight of the composition, derived in an enzymatically-catalyzed reaction from saturated or unsaturated, straight or branched $C_8$-$C_{22}$ fatty acids of vegetable oils, and useful, inter alia, in biofuels, such as biodiesel, and as an additive for improving the lubricating performance of fuel compositions.

6 Claims, No Drawings

US 7,799,544 B2

COMPOSITIONS WHICH CAN BE USED AS BIOFUEL

CROSS-REFERENCE TO RELATED APPLICATIONS

This application is filed under 35 U.S.C. §371 claiming priority from Application PCT/EP2006/000121, filed on Jan. 10, 2006, the entire contents of which are incorporated herein by reference.

FIELD OF THE INVENTION

This invention relates generally to glycerides and, more particularly, to compositions containing fatty acid esters and partial glycerides, to their production, for example, by enzymatic catalysis, and to their use as a biofuel.

BACKGROUND AND RELATED ART

Hydrocarbon-based fuels, for example, various petroleum fractions, heating oils, gasoline, diesel, kerosene, etc., generally contain numerous additives. Besides corrosion inhibitors and lubricity additives, these additives may include flow improvers or compounds which improve the emission levels of gases, such as CO, $CO_2$ and/or $NO_x$.

As a result of Directive 2003/30/EC, Article 3.1 (b), the European Parliament decreed that, effective Dec. 31, 2005, all diesel fuels should contain 2% biofuel. This percentage is supposed to increase to 5.75% by Dec. 31, 2010. In Article 2.2 of this Directive, biofuel is defined as bioethanol, rapeseed oil methyl ester (RSME), biogas, biomethanol, biodimethylether, biohydrogen, synthetic biofuels and purely vegetable oils.

In general, rapeseed oil methyl ester (RSME) is used as biodiesel. It is already possible that engines are being powered by pure biofuel under the EU Directive. However, it is likely that up to 2% RSME is being added to normal diesel in order to comply with the EU Directive.

This RSME is produced by converting the natural triglyceride into a methyl ester, or even an ethyl ester. The by-product of this process is crude free glycerol. Because 100 kg free glycerol is formed in the production of 1 metric ton of RSME as biodiesel, the amount of glycerol available increases with the increasing production of RSME. Since there is a limited market for glycerol, which market is already satisfied by existing production, glycerol disposal problems arise. This situation makes the normal production route economically unattractive and potentially limits the use of this route for producing biodiesel, as glycerol can no longer be factored in as additional profit.

Glycerol has to be removed from the diesel and biodiesel being produced, as a high glycerol level adversely affects the combustion performance of those fuels. One reason for this is the poor solubility of glycerol in the rapeseed oil methyl ester generally used as biodiesel. An excessive concentration of glycerol in the methyl ester leads to the formation of a heavy glycerol phase, which can settle, for example, in the fuel tank. If such a glycerol phase is injected into the engine, performance is reduced, and the wear on individual engine components is potentially increased.

Various enzymatic routes suitable for the production of monoglycerides have been described in the literature, including: 1) enzymatic synthesis starting from fatty acid and glycerol; 2) enzymatic glycerolysis starting from triglyceride and glycerol, which corresponds to the chemical process; and 3) the 1,3-regioselective hydrolysis or alcoholysis of triglyceride. Summaries of these processes may be found, for example, in Recent Res. Devel. Oil Chem., 3 (1999), 93-106; and Hydrolases in Organic Synthesis, Wiley-VCH (1999), eds. Bornscheuer & Kazlaukas.

Enzymes increasingly are being used as catalysts in chemical and biochemical syntheses. Thus, in many cases, hydrolases, more especially lipases (EC 3.1.1.3), are already being used for lipolysis or transesterification in industrial processes by virtue of the often relatively mild reaction conditions. These enzymes are produced by various microorganisms, then to isolate them, fermentation of the microorganisms is followed by an expensive purification process. The effectiveness of these catalysts is often offset by the high costs of production and isolation, driving research groups to constantly strive to increase the yields of these enzymes and/or the productivity of them. The standard chemical method for producing monoglycerides involves the base-catalyzed glycerolysis of triglycerides, a yield of 40 to 60% monoglyceride, based on the total glycerides, typically being obtained. Further enrichment to a >90% monoglyceride content is achieved by physical separation techniques, such as molecular distillation or crystallization.

WO 90/13656 and WO 90/04033 (both Enzytech, Inc.) and U.S. Pat. No. 5,935,828 and U.S. Pat. No. 5,316,927 (both Zaks et al.) describe the production of monoglycerides by enzymatic alcoholysis with various alcohols and a little water in the mixture. Lipases are used in powder form or are immobilized. In the Examples, the alcohol component is present in a 20-fold excess, and lipases are used in quantities of ca. 20%, by weight, based on the triglyceride.

WO 91/16441, WO 91/16442 (both Procter & Gamble) and U.S. Pat. No. 5,116,745 (Mazur et al.) describe processes in which a mixed regioselective alcoholysis and hydrolysis to 1,2-diglycerides and 2-monoglycerides, using lipases, is carried out in the presence of a solvent, an alcohol and an aqueous buffer.

EP 0 407 959 A2 (Lion Corporation) describes a process for the production of monoester using a thermostable, immobilized lipase in the presence of secondary or tertiary alcohols as solubilizers.

WO 02/06505 A1 (Nippon Suisan Kaisha Ltd.) describes regioselective alcoholysis using an immobilized lipase, a large excess of alcohol and high concentrations of enzyme, followed by re-esterification of the monoglyceride.

JP 03108489 and JP03187385 (Meito Sangyo Co. Ltd.) describe the regioselective hydrolysis of triglycerides with an alkaline lipase in the presence of alkaline salts. The lipase used is only active under alkaline conditions.

JP 03103499 (Meito Sangyo Co. Ltd.) describes the regioselective alcoholysis of PUFA triglycerides with isobutanol in the presence of an alkaline lipase.

Although the enzymatic production of partial glycerides has already been widely described, solvents are required in all the above-cited documents, the water of reaction has to be removed at considerable expense, and the special lipases are used that are not commercially available on an industrial scale.

Now, a first objective of this invention was to provide a biofuel which would comply with the guidelines of the European Parliament and in which the glycerol would be present as a derivative, resulting in very little free glycerol being formed as a by-product in the production process. Thus, the production process would be environmentally friendly and economical. A second objective of this invention was to find an inexpensive enzymatic or chemical variant that would increase the yield of monoglycerides and diglycerides from polyol esters, such as triglycerides, for example, and where the enzyme content in the enzymatic alcoholyses would be kept to a minimum.

BRIEF SUMMARY OF THE INVENTION

The instant invention is directed to a composition comprising $C_1$-$C_8$ alkyl ester and partial glycerides, with a free glycerol content of <2%, by weight, produced by enzyme-catalyzed reactions, where the enzymes are activated by alkaline inorganic salts, from saturated or unsaturated, straight- or branched-chain fatty acids obtainable from vegetable oils, and useful as biofuels.

DETAILED DESCRIPTION OF THE INVENTION

The present invention is directed to a composition containing alkyl esters, with a $C_{1-8}$ alkyl group, and partial glycerides, with a free glycerol content of, at most, 2%, by weight, based on the total weight of the composition.

It has surprisingly been found that compositions which contain the above-mentioned components in the mixture and, at most, 2%, by weight, free glycerol solve the objectives addressed by the invention in an outstanding manner. A maximum glycerol content of 1.3%, by weight, is preferred, and a maximum glycerol content of 1.0%, by weight, is particularly preferred, the evaluation being according to GC analysis, and the values for glycerol having to be calibrated in view of the strong absorption.

In one particular embodiment, the composition contains methyl and/or ethyl esters as the alkyl esters.

In another particular embodiment, the composition has a partial glyceride content of at least 10%, by weight, and/or a triglyceride content of, at most, 5%, by weight, and/or an acid value of, at most, 5, based on the total quantity of the composition. A monoglyceride content of at least 25%, by weight, is preferred.

In still another particular embodiment, the composition contains methyl and/or ethyl esters, monoglycerides and diglyceride in the following quantities:

methyl and/or ethyl esters: 30 to 70%, by weight, preferably 55 to 60%, by weight;

monoglyceride: 10 to 35%, by weight, preferably 25 to 33%, by weight; and diglyceride: 1 to 30%, by weight, preferably 1 to 20%, by weight.

The percentages by weight are evaluated via the %-areas in GC analysis.

An additional particular embodiment is compositions in which the alkyl esters and partial glycerides represent fatty acid esters of saturated or unsaturated, linear or branched fatty acids with a $C_{8-22}$ alkyl group. Fatty acid esters obtainable from vegetable oils, such as, for example, linoleate, oleate, palmitate, stearate and/or pelargonate, are particularly preferred for the purposes of the invention. Unsaturated representatives are, for example, lauroleic, myristoleic, palmitoleic, petroselaidic, oleic, elaidic, ricinoleic, linoleic, linolaidic, linolenic, gadoleic, arachidonic and erucic acid esters. Mixtures of the methyl and/or ethyl esters of these acids are also suitable.

Preferred oils for obtaining the fatty acid esters include sunflower oil, rapeseed oil, thistle oil, soybean oil, linseed oil, peanut oil, tallows, olive oil, castor oil, palm oil, palm oil fractions, such as palm olein and palm stearin, yatropha oil, coconut oil and palm kernel oil.

Peanut oil contains, on average (based on fatty acid), 54%, by weight, oleic acid, 24%, by weight, linoleic acid, 1%, by weight, linolenic acid, 1%, by weight, arachic acid, 10%, by weight, palmitic acid and 4%, by weight, stearic acid. Its melting point is 2 to 3° C.

Linseed oil typically contains 5%, by weight, palmitic acid, 4%, by weight, stearic acid, 22%, by weight, oleic acid, 17%, by weight, linoleic acid and 52%, by weight, linolenic acid. It has an iodine value of 155 to 205, a saponification value of 188 to 196 and a melting point of ca. −20° C.

Olive oil mainly contains oleic acid. Palm oil contains ca. 2%, by weight, myristic acid, 42%, by weight, palmitic acid, 5%, by weight, stearic acid, 41%, by weight, oleic acid, and 10%, by weight, linoleic acid as fatty acid components.

Rapeseed oil typically contains ca. 48%, by weight, erucic acid, 15%, by weight, oleic acid, 14%, by weight, linoleic acid, 8%, by weight, linolenic acid, 5%, by weight, eicosenoic acid, 3%, by weight, palmitic acid, 2%, by weight, hexadecenoic acid and 1%, by weight, docosadienoic acid as fatty acid components. Rapeseed oil from new plants has higher levels of the unsaturated acids. Typical fatty acid levels in rapeseed oil are erucic acid 0.5%, by weight, oleic acid 63%, by weight, linoleic acid 20%, by weight, linolenic acid, 9%, by weight, eicosenoic acid, 1%, by weight, palmitic acid, 4%, by weight, hexadecenoic acid, 2%, by weight, and docosadienoic acid, 1%, by weight.

80 to 85%, by weight, of castor oil consists of the glyceride of ricinoleic acid. Castor oil also contains ca. 7%, by weight, oleic acid glycerides, 3%, by weight, linoleic acid glycerides and ca. 2%, by weight, palmitic and stearic acid glycerides.

Soybean oil contains 55 to 65%, by weight, based on total fatty acids, of polyunsaturated acids, more particularly, linoleic and linolenic acid. The situation is similar with sunflower oil of which the typical fatty acid spectrum, based on total fatty acids, is ca. 1%, by weight, myristic acid, 3 to 10%, by weight, palmitic acid, 14 to 65%, by weight, oleic acid and 20 to 75%, by weight, linoleic acid.

All the above-mentioned figures relating to the percentage of fatty acid in the triglycerides are known to depend on the quantity of the raw materials and may vary accordingly.

The fatty acid composition in the mixture results from the particular fatty acid composition of the vegetable oils used and the particular quality of the raw materials from which the methyl and/or ethyl esters and the monoglycerides are produced.

The present invention also relates to a process for the production of biofuel in which triglycerides are enzymatically reacted with an esterase activated by the addition of alkaline salts, the reaction being carried out in the presence of alcohols containing 1 to 8 carbon atoms.

It has surprisingly been found that the addition of alkaline salts may activate esterases so that an increased yield of monoglycerides compared with known processes may be achieved in the alcoholysis of triglycerides.

In the process according to the invention, a triglyceride is split into a 2-monoglyceride and two fatty acid esters in the presence of an alcohol. In this process, more than 90% of the glycerol remains chemically bound in the product and the small concentrations of free glycerol remain dissolved in a single phase in the product. Accordingly, in contrast to conventional biodiesel production, no glycerol is formed as a by-product in the process according to the invention, allowing the quantity of raw material (oil) required to be reduced accordingly.

The reaction may be carried out very economically through the use of small quantities of esterase, preferably lipase. The reaction is directly carried out with the enzyme concentrate in the presence of an added alkaline inorganic salt which strongly activates the enzyme. In this way, a high conversion is achieved with a small quantity of enzyme, even without stabilization of the enzyme by immobilization, and there is no need for the addition of solvents.

The alcoholysis is carried out at temperatures of 10° C. to 40° C., preferably at 10° C. to 30° C. and more particularly—to maintain optimal regioselectivity and activity—at a temperature of 15° C. to 25° C. The reaction is carried out with a water content, including the water content of the liquid enzyme preparation, of 0.1 to 10%, by weight, preferably 0.1 to 5%, by weight, and more particularly, 0.1 to 2%, by weight, based on the quantity of triglyceride. Although the reaction may also be carried out with higher water contents, the content of free fatty acids formed is increased in that case (high levels of free fatty acid being undesirable because, when used in biodiesel, they can have a corrosive effect on engine parts at high temperatures).

The reaction time is preferably 12 to 48 hours, depending on the enzyme concentration used. In a preferred embodiment, all the reactants are mixed and the reaction is initiated by the addition of the enzyme preparation.

The alcohol component containing 1 to 8 carbon atoms, preferably methanol and/or ethanol, preferably ethanol, is added either completely at the beginning of the reaction or over the duration of the reaction. The quantity of alcohol used is variable between a minimum of 2 mols alcohol to 1 mol oil and a maximum of 50%, by weight, alcohol and 50%, by weight, oil in the mixture.

In another step of the process according to the invention, the esterase may be deactivated by heat and the precipitated esterase may then optionally be filtered off, in which case not only the precipitated esterase, but also additives or formulation ingredients of the enzyme preparation used may be removed.

The following optional steps may be added to the process according to the invention:
   addition of water-adsorbing agents during the enzymatic reaction to suppress the formation of free acids;
   filtration of the reaction mixture through filter aids to remove additives or ingredients of the enzyme formulation; and/or
   refinement of the product mixture with water to remove free glycerol which is formed in small quantities as a by-product.

As a result of the emulsifying character of the monoglycerides formed, any fatty acids formed, free glycerol and/or small amounts of water present remain dissolved in a single phase in the product.

In one particular embodiment of the invention, alcohol and/or water is/are completely or partly removed, preferably by distillation. Any free glycerol still present—having been formed in small quantities as a by-product—may also be removed in the distillation step. Tests have shown that, even after the blending of the biodiesel with diesel, alcohol, water and/or glycerol may remain dissolved in the diesel by virtue of the emulsifying effect of the monoglyceride.

Experimental data have shown that the addition of small quantities of alkaline inorganic salts greatly increases the enzyme activity of the esterases. In particular, non-immobilized lipases are activated by the alkaline salts.

The commercially-obtainable liquid preparation is preferably used in a concentration of 0.05 to 2%, by weight, based on the weight of triglyceride used. These commercially-obtainable liquid enzyme preparations have an enzyme activity of on average 100,000 U/ml. One enzyme unit, "U", is defined as the quantity of enzyme which reacts with one micromol of substrate per minute. In the process according to the invention, alkaline inorganic salts selected from the group consisting of hydroxides, carbonates and phosphates of sodium, potassium, calcium, magnesium and ammonium, predissolved in water, are preferably used to activate the esterase. According to the invention, the quantity of alkaline inorganic salts for activating the esterase is between 0.00001 and 1%, by weight, and preferably between 0.0001 and 0.2%, by weight, based on the weight of triglyceride used. The quantity of basic additive used depends on the quantity of buffered liquid enzyme preparation used and on the strength of the base employed. Where NaOH and <0.5% liquid enzyme preparation are used, the concentration of basic additive is in the lower range, e.g., up to about 0.2%, by weight, based on the weight of the triglyceride used; where $Na_2CO_3$ and 2% liquid enzyme preparation are used, the quantity of basic additive is in the upper concentration range, e.g., up to about 1%, by weight, based on the weight of the triglyceride used.

Surprisingly, the strongest activation of the *Thermomyces lanugenosus* lipase was achieved when salts such as, for example, trisodium phosphate, sodium carbonate, sodium hydroxide or ammonium hydroxide were added to the commercially-obtainable liquid enzyme preparation in quantities of 0.0001 to 0.2%, by weight (based on the triglyceride content). Surprisingly, a faster monoglyceride synthesis rate was achieved than with a *Thermomyces* lipase adsorbed onto polypropylene. The activation of the lipase is so strong that it cannot be explained by the pH shift in the reaction medium alone. If the *Thermomyces lanugenosus* lipase is used in immobilized form under the same conditions, there is no sign of equally strong activation by the addition of salts. This strong activation is very surprising as it is generally accepted that a high activity level may only be achieved in the low-water medium with lipases fixed to a carrier. The strong activation eliminates the need for elaborate immobilization processes and leads to a simple process and equipment installation. In addition, measurement of the pH value of the reacted product mixture shows that the pH is in the neutral to mildly acidic range which makes enzyme activation by pH shift alone improbable.

The present invention also relates to a process for the production of monoglycerides in which triglycerides are enzymatically reacted with an immobilized and/or chemically-modified esterase in the presence of alcohols containing 1 to 8 carbon atoms.

It has surprisingly been found that the composition according to the invention may also be produced in an outstanding manner by this enzymatic process. In this process, too, more than 90% of the glycerol remains chemically bound in the product and the small concentrations of free glycerol remain dissolved in a single phase in the product. Accordingly, in contrast to the conventional production of biodiesel, no glycerol is formed as a by-product in the enzymatic process according to the invention either, allowing the quantity of raw material (oil) required to be distinctly reduced accordingly. By repeatedly using the immobilized and/or chemically modified esterase, preferably lipase, the reaction may be carried out very economically, without the need for (additional) solvents.

The alcoholysis is carried out at temperatures of from 10° C. to 60° C., preferably at from 10° C. to 40° C., and more particularly—to maintain optimal regioselectivity and activity—at a temperature of from 15° C. to 30° C. The reaction is carried out with a water content of 0.1 to 10%, by weight, preferably 0 to 5%, by weight, and more particularly 0 to 2%, by weight, based on the quantity of triglyceride used.

Although the reaction may also be carried out with higher water contents, the content of free fatty acid formed is increased in that case (as explained earlier, high levels of free fatty acid being undesirable because, when used in biodiesel, they may have a corrosive effect on engine parts at high temperatures).

The reaction time is preferably 1 to 48 hours, depending on the enzyme concentration used. In a preferred embodiment, all the reactants are mixed and the reaction is initiated by the addition of the enzyme preparation.

The alcohol component, preferably methanol and/or ethanol, preferably ethanol, is added either completely at the beginning of the reaction or over the duration of the reaction. The quantity of alcohol used is variable, between a minimum of 2 mols alcohol to 1 mol oil and a maximum of 50%, by weight, alcohol and 50%, by weight, oil in the mixture.

In another step of the process according to the invention, the esterase may be filtered off. As explained earlier, the following optional steps may be added to the process according to the invention:
  addition of water-adsorbing agents during the enzymatic reaction in order to suppress the formation of free acids;
  filtration of the reaction mixture through filter aids to remove ingredients of the enzyme formulation or insoluble components of the oil used; and/or
  refinement of the product mixture with water to remove free glycerol, which is formed in small quantities as a by-product.

Again, as a result of the emulsifying character of the monoglycerides formed, any fatty acids formed, free glycerol and small amounts of water present remain dissolved in a single phase in the product.

In one particular embodiment of the invention, alcohol or/and water is/are completely or partly removed, preferably by distillation. Any free glycerol still present—having been formed in small quantities as a by-product—may also be removed in the distillation step. Tests have shown that, even after the blending of the biodiesel with diesel, alcohol, water and/or glycerol may remain dissolved in the diesel by virtue of the emulsifying effect of the monoglyceride.

Various carrier materials suitable for the formation of enzymes may be used for the process according to the invention. Plastics, mineral carriers or resins, such as Amberlite™ 16 (Rohm & Haas), Celite or Accurel MP 1000 (Membrana), for example, which bind the esterases through hydrophobic interactions, may be used as carriers. Other suitable carriers include ion exchangers, such as Dowex® Marathon WBA (Dow Chemical) or Duolite™ A 568 (Rohm & Haas), for example, which bind the esterases through ionic and, in part, hydrophobic interactions, as well as carriers that are capable of binding the esterases through chemically reactive groups, such as Eupergit (Degussa) for example.

Chemical modifications are also suitable for adapting the esterases to the reaction system. Hydrophobic modifications, such as coating with surfactants for example, or chemical modification with fatty aldehydes may be used. Stabilization of the esterases through crosslinking, for example by glutaraldehyde, DMA or EDC, is also suitable.

A combination of chemical modification and immobilization is also suitable for adapting the esterases to the reaction system. In this case, either the esterases may first be immobilized and then modified on a carrier or esterases which have already been chemically modified are immobilized.

The esterases to be used in the enzymatic processes according to the invention are preferably those which originate from an organism selected from the group consisting of *Thermomyces lanugenosus, Candida antarctica A, Candida antarctica B, Rhizomucor miehei, Candida cylindracea, Rhizopus javanicus, Porcine pancreas, Aspergillus niger, Candida rugosa, Mucor javanicus, Pseudomonas fluorescens, Rhizopus oryzae, Pseudompnas* sp., *Chromobacterium viscosum, Fusarium oxysporum* and *Penicilium camemberti*. Esterases from *Thermomyces lanugenosus*, also called *Humicola lanuginosa* are particularly preferred.

Esterases are enzymes that catalyze the formation and hydrolysis of esters; as hydrolases, they split their respective substrates with incorporation of the elements of water. These esterases include, for example, the fat-splitting lipases which represent the preferred esterases for the process according to the present invention. The use of 1,3-regiospecific lipases is particularly preferred for the process according to the invention, these lipases being distinguished by the fact that they preferentially split off the fatty acids at the 1- and 3-positions of triglycerides. In principle, any 1,3-regioselective lipase or esterase in free or immobilized form may be used for the process according to the invention. The lipase of *Thermomyces lanugenosus* (manufacturer: Novozymes, under the names: Lipozyme TL 100 I or Lipoplase 100 EX) has proven to be particularly preferred for the process according to the invention.

The present invention also relates to a process for the production of monoglycerides in which triglycerides are chemically reacted in the presence of alcohols containing 1 to 8 carbon atoms. In this process, the alcohols are used in a molar concentration which is lower than the molar concentration of the glyceride-bonded fatty acid. It has surprisingly been found that the composition according to the instant invention may be produced by this process. In this process, at least a large part of the glycerol present in the triglyceride remains bound in the product, in order that less glycerol is formed than in the conventional production of biodiesel.

In the process according to the invention, either alkaline catalysts or strongly acidic catalysts are used in a low-pressure transesterification. High-pressure transesterifications in the presence of a chemical catalyst are also part of the process.

Preferred catalysts for the alkaline low-pressure transesterification with homogeneous catalysis are the salts of alcohols containing 1 to 8 carbon atoms with monovalent cations, the sodium and potassium salts of methanol and ethanol being particularly preferred. Preferred catalysts for the alkaline low-pressure transesterification in heterogeneous catalysis are carbonates and oxides such as, for example, sodium carbonate or calcium oxide. The catalysts are used in a concentration of 0.01%, by weight, to 5%, by weight, and preferably in a concentration of 0.1%, by weight, to 1%, by weight. The alkaline catalysts may be prepared in situ from water-free NaOH or KOH and the corresponding alcohol. The transesterification is carried out at a temperature of 40° to 120° C. and under a pressure of at most 2 bar, preferably under a pressure of at most 1.2 bar. At the end of the reaction, the catalyst is neutralized by the addition of an acid such as, for example, citric acid, phosphoric acid, hydrochloric acid or sulfuric acid and is removed by separation. The reaction time is preferably 0.1 to 10 hours, depending on the catalyst concentration used and the reaction temperature.

Preferred catalysts for the acidic low-pressure transesterification with homogeneous catalysis are mineral acids, more especially sulfuric acid, or aliphatic and aromatic sulfonic acids. The catalysts are used in a concentration of 0.01%, by weight, to 5%, by weight. The transesterification is carried out at a temperature of 40° to 160° C. under a pressure of at most 5 bar. At the end of the reaction, the catalyst is neutralized by the addition of an alkali such as, for example, aqueous NaOH or KOH and removed by separation. The reaction time is preferably 0.5 to 25 hours, depending on the catalyst concentration used and the reaction temperature.

Preferred catalysts for the high-pressure transesterification are metal salts or metal soaps, preferably salts or soaps of zinc such as, for example, zinc acetate or zinc stearate in a concentration of 0.01%, by weight, to 1%, by weight. The transesterification is carried out at a temperature of 120° to 250° C. under a pressure of at most 20 to 200 bar. At the end of the reaction, the catalyst is removed by filtration. The reaction time is preferably 0.1 to 5 hours, depending on the catalyst concentration used and the reaction temperature.

In the process according to the invention, the partial chemical transesterification may be carried out as a batch reaction or as a continuous reaction. In the continuous variant, the alcohol component may either be transported as a gas circulated countercurrent to the oil or, alternatively, may be transported in co-current as a single phase with the oil under high-pressure conditions or low-pressure conditions. In a preferred embodiment, all the reactants are mixed and the reaction is initiated by the addition of the catalyst. The alcohol component, preferably methanol and/or ethanol, more preferably ethanol, is added either completely at the beginning of the reaction or over the duration of the reaction. The quantity of alcohol used is variable between a minimum of 10 mol-% alcohol and a maximum of 30 mol-% alcohol, based on the quantity of oil used in the mixture.

In another step of the process according to the invention, the catalyst may be filtered off or neutralized and washed out after the reaction. The following optional steps may be added to the process according to the invention:

addition of water-adsorbing agents during the reaction in order to suppress the formation of free acids;

filtration of the reaction mixture through filter aids to remove the catalyst or insoluble components of the oil used; and/or refinement of the product mixture with water to remove free glycerol which is formed as a by-product.

As explained above, any fatty acids formed, free glycerol and small amounts of water present remain dissolved in a single phase in the product as a result of the emulsifying character of the monoglycerides formed.

In one particular embodiment of the invention, alcohol and/or water is/are completely or partly removed, preferably by distillation. Any free glycerol still present—having been formed in small quantities as a by-product—may also be removed in the distillation step.

Acid-containing fats and oils may readily be used in the described acid-catalyzed low-pressure process and in the chemically catalyzed, high-pressure process.

Triglycerides from fats and oils which have a high percentage content of mono- and/or polyunsaturated fatty acids and which are selected from the group consisting of sunflower oil, rapeseed oil, thistle oil, soybean oil, linseed oil, peanut oil, tallows, olive oil, castor oil, palm oil, yatropha oil, coconut oil, palm kernel oil and old oils, including for example, used frying fat, are preferably used in the process according to the invention. The fats and oils may be used in refined or unrefined form in the process according to the invention. Acid-containing fats and oils may readily be used in the process according to the invention.

Alcohols containing 1 to 8 carbon atoms are preferably used as alcohol components for the process according to the invention. These alcohols may have linear or branched carbon chains and are preferably primary or secondary alcohols, preferably selected from the group consisting of methanol, ethanol, 1-propanol, isopropanol, 1-butanol, sec. butanol., tert. butanol, 1-pentanol, 1-hexanol, 1-heptanol, 1-octanol, and 2-ethylhexanol. Particularly preferred alcohol components are methanol, ethanol and/or 1-propanol. Methanol and ethanol or mixtures thereof are particularly preferred, ethanol being more particularly preferred. The ethanol used is preferably obtainable from biological sources, for example from the fermentation of carbohydrates.

The alcohol content is preferably 10 to 50%, by weight, or 10 to 30 mol-% in the chemical process, based on the triglyceride used, more preferably 15 to 40%, by weight, or 15 to 25 mol-%, in the chemical process. The monoglyceride content is dependent on the quantity of alcohol used.

The present invention also relates to a composition obtainable by the process according to the invention. The composition thus obtained, which consists mainly of alcohol, alkyl ester, monoglyceride and diglyceride, may be directly added to diesel fuel, with any fatty acids formed, free glycerol and small amounts of water present dissolved in a single phase in the product. Traces of water are effectively bound and do not adversely affect the combustion process, while the monoglycerides formed enhance the lubricating properties. The effect of the components in their mixed form in the composition according to the invention may result in the glycerol present being more effectively burned in the combustion process. To reduce the flash point, alcohol may be completely or partly removed from the composition produced in accordance with the invention, for example by distillation, before it is added to the diesel.

Accordingly, the present invention also relates to a fuel composition containing 90 to 99.5%, by weight, gas oil and 0.5 to 10%, by weight, and preferably 2 to 6%, by weight, of a composition according to the invention or of a composition obtainable by the process according to the invention.

In the context of the invention, "gas oil" is meant to encompass every possible fraction of petroleum in both the additive-containing and the additive-free state. Gas oil in the context of the present invention is preferably understood to be diesel fuel. Additives which are present in the gas oil mentioned in its additive-containing state and which may be present in addition to the compositions according to the invention, are additives selected from the group consisting of conductivity improvers, cetane number improvers, CFPP/CP improvers, defoamers, lubrication improvers, corrosion inhibitors and dehazers. These additives are used in the usual concentrations and are well-known in the oil industry.

The potential applications of this gas oil—both in the additive-containing and in the additive-free state—are included in the definition. This includes both uses in transportation, for example, as diesel for engines, and uses outside transportation, for example, as heating oil, tractor oil, diesel fuel for mobile diesel engines, marine bunker oils or the like. The distillation range of the gas oil fractions extends from 140° to 400° C.

Diesel fuels are obtained from its petroleum base by cracking or from tars which are obtained in the low-temperature carbonization of lignite or coal. Diesel fuels are poorly flammable mixtures of liquid hydrocarbons which are used as fuels for constant-pressure or compression-ignition engines (diesel engines) and which consist mainly of paraffins with admixtures of olefins, naphthenes and aromatic hydrocarbons. Their composition is variable and depends in particular on the production method used to produce them. Typical products have a density of 0.83 to 0.88 g/cm$^3$, a boiling point of 170° to 360° C. and a flash point of 70° to 100° C.

The present invention also relates to the use as a biofuel of the composition according to the invention which contains alkyl esters with a $C_{1-8}$ alkyl group and partial glycerides that has a free glycerol content of at most, 2% by weight, based on the total quantity of the composition. It also relates to the preferred embodiments of the composition obtainable by the process according to the invention used as a biofuel.

The present invention provides a biofuel in which only small quantities of free glycerol are present as a by-product. More particularly, the enzymatic reaction of pure vegetable oil and bioalcohol gives a mixture of alkylester and partial glycerides, which may be used as a biofuel or as an additive in compliance with European Directive 2003/30/EC. In addition to the use of vegetable oil, the ethanol is also preferably produced from renewable raw materials, resulting in a biofuel that has the advantages of its raw materials coming from renewable sources.

Besides its production with few by-products, another advantage of the biofuel according to the instant invention lies in the introduction of additional oxygen into the combustion path which reduces emissions. Also, the additional lubricating effect of the partial glycerides eliminates the need to use lubricity improvers. In contrast to the known production of rapeseed oil methyl ester, the first production process is energy-saving because it is purely enzymatic and does not involve major purification of the end product. Tests have shows that the low-temperature behavior of commercially available diesels is not adversely affected by blending with the composition according to the invention, particularly the cold filter plugging point (CFPP), an important property, is not adversely affected. Slight clouding of the mixture, but no precipitation or phase separation, was observed at temperatures around −20° C., the mixture remaining thinly liquid and pumpable. No changes occurred even during storage at 4° C.

The present invention also relates to the use of the composition according to the invention containing alkyl esters with a $C_{1-8}$ alkyl group and partial glycerides and, more particularly, methyl and/or ethyl esters, monoglycerides and methanol and/or ethanol, which has a glycerol content of at most 2% by weight, based on the total quantity of the composition. This invention also relates to the use of preferred embodiments of the composition, obtainable by the process according to the invention as an additive in fuel compositions, preferably in quantities of 0.5 to 10% by weight and more particularly in quantities of 1 to 5% by weight. In a particularly preferred embodiment, the composition according to the invention is used as an additive for improving the lubricating performance of fuel compositions.

The use of various additives for fuels is known from the literature. Monoglycerides and other partially-esterified or -etherified polyols (for example, even glycol monoesters) are added as a diesel additive because they have a good lubricating effect. Patent applications which describe such additives include, for example, EP 0 721 492 (Infineum USA L.P.), WO 0119941 (Fina Research S.A.) and WO 0063322 (Pure Fuels USA Inc.).

More particularly, glyceride mixtures with a high percentage of monoglyceride have good lubricating properties. Thus, it has been found that the monoglycerides produced by the process according to the invention may also be used as fuel additives in diesel fuel showing good lubricating properties in such use.

The regiospecific fatty acid composition of the naturally-occurring oils may be utilized in the enzymatic processes according to the invention. The monoglyceride fraction mainly contains the fatty acid composition which is to be found in the 2-position of the oils. With most naturally occurring oils, the more highly unsaturated fatty acids are preferably bound in the 2-position. In this way, monoglycerides with a high linoleic acid content may be produced, for example, from sunflower or thistle oil. These monoglycerides have a reduced solidification point which is particularly important for the use of monoglycerides as a diesel additive. A monoglyceride with a high oleic acid content may be obtained, for example, from palm oil.

In the context of the present invention, fuel compositions are understood to be any energy-providing fuels of which the free combustion energy is converted into mechanical work. This includes all types of motor and aircraft fuels which are liquid at room temperature and normal pressure. Motor fuels, for example for automobile and truck engines, generally contain hydrocarbons, for example gasoline or higher-boiling petroleum fractions. The fuel compositions according to the invention are preferably diesel oil.

EXAMPLES

Example 1

Regioselective Alcoholysis with Various Enzymes in Free and Immobilized Form 16 mixtures consisting of 20 g rapeseed oil and 2.5 g ethanol were placed in glass beakers equipped with magnetic stirrers. 0.25 g water was added with stirring to mixtures 1 to 9, 15 and 16; 0.5 g water was added to mixtures 10 to 14. Lipases in free and immobilized form as listed in the following Table were then added, and the mixtures were incubated with stirring for 24 hours, another 2.5 g ethanol being added after 5 hours. The alcoholysis of mixtures 1 to 14 was carried out at room temperature on a multistirrer plate. Mixtures 15 and 16 were incubated at 45° C. on a shaker. After 24 hours, samples were taken and the content of glycerides and ethyl esters was analyzed by gas chromatography. The results were evaluated as percentage areas. Small amounts of fatty acid formed are contained in the ethyl ester area.

The immobilizates of mixtures 1 to 3, 15 and 16 were acquired in immobilized form direct from the manufacturer. The immobilizates of mixtures 4 to 8 were prepared by adsorption onto Accurel® MP 1000 (Membrana). To this end, Accurel MP 1000 was incubated for 1 hour in 10 ml ethanol. After the ethanol had been decanted off, 10 g water and 0.5 g of each lipase preparation were added. The mixture was incubated overnight at room temperature. The immobilizate was then separated by filtration and dried for 24 hours at room temperature on sheets of paper.

| Mixture | Enzyme | Manufacturer | Organism | Form |
| --- | --- | --- | --- | --- |
| 1 | 1 g Novozym 435 | Novozymes | C. antarctica B | Immobilizate |
| 2 | 1 g Lipozym RM IM | Novozymes | R. miehei | Immobilizate |
| 3 | 1 g Lipozym TL IM | Novozymes | T. lanugenosus | Immobilizate |
| 4 | 1 g Lipase FAP 15/MP 1000 | Amano | R. oryzae | Immobilizate |
| 5 | 1 g Lipase A/MP 1000 | Amano | A. niger | Immobilizate |

-continued

| | | | | |
|---|---|---|---|---|
| 6 | 1 g Lipase M/MP 1000 | Amano | M. javanicus | Immobilizate |
| 7 | 1 g Lipase L115/MP 1000 | Biocatalysts | Porcine pancreas | Immobilizate |
| 8 | 1 g Lipomod 36/MP 1000 | Biocatalysts | R. javanicus | Immobilizate |
| 9 | 0.5 g Lipolase | Novozymes | T. lanugenosus | Free |
| 10 | 0.5 g Lipase FAP 15/MP 1000 | Amano | R. oryzae | Free |
| 11 | 0.5 g Lipase A/MP 1000 | Amano | A. niger | |
| 12 | 0.5 g Lipase M/MP 1000 | Amano | M. javanicus | |
| 13 | 0.5 g Lipase L115/MP 1000 | Biocatalysts | Porcine pancreas | |
| 14 | 0.5 g Lipomod 36/MP 1000 | Biocatalysts | R. javanicus | |
| 15 | 1 g Novozym 435 | Novozymes | C. antarctica B | Immobilizate |
| 16 | 1 g Lipozym RM IM | Novozymes | R. miehei | Immobilizate |

| Mixture | % Ethyl ester | % Monoglyceride | % Diglyceride | % Triglyceride |
|---|---|---|---|---|
| 1 | 18.2 | 1.4 | 5.0 | 75.4 |
| 2 | 39.3 | 16.2 | 14.5 | 29.5 |
| 3 | 62.7 | 23.5 | 10.9 | 0.5 |
| 4 | 58.5 | 29.6 | 9.6 | 0.0 |
| 5 | 5.2 | 1.6 | 4.6 | 88.6 |
| 6 | 41.7 | 16.5 | 27.7 | 14.1 |
| 7 | 82.4 | 6.8 | 7.0 | 2.9 |
| 8 | 57.7 | 32.7 | 8.3 | 0.0 |
| 9 | 15.9 | 4.1 | 14.8 | 65.2 |
| 10 | 0.0 | 0.0 | 2.1 | 96.2 |
| 11 | 2.0 | 0.4 | 1.6 | 96.0 |
| 12 | 3.4 | 0.0 | 2.4 | 94.2 |
| 13 | 2.2 | 0.4 | 2.3 | 95.1 |
| 14 | 3.3 | 0.0 | 2.8 | 93.9 |
| 15 | 41.0 | 0.0 | 2.2 | 55.8 |
| 16 | 3.7 | 0.0 | 2.3 | 94.0 |

Result:

It was found that all the immobilized lipases tested showed alcoholysis activity and are therefore suitable in principle for the production of the compositions according to the invention. Particularly good reactions were achieved with immobilized *Thermomyces*, *Rhizopus* and *Porcine Pancreas*; moderate conversion rates were observed with *Rhizomucor* and *Mucor* lipases. Under the test conditions, the free lipases showed distinctly poorer conversion rates. Only free lipase from *Thermomyces* showed significant product formation.

Example 2

Regioselective Alcoholysis of Sunflower Oil with Non-immobilized Lipases 6 mixtures consisting of 40 g sunflower oil and 10 g ethanol were placed in glass beakers equipped with magnetic stirrers. 0.4 g water was added with stirring. 40 mg solid $Na_3PO_4 \times 12H_2O$ were added to mixtures 2, 4 and 6. 0.4 g lipolase (*Thermomyces lanugenosus* lipase, liquid preparation) was added to mixtures 1 and 2, 0.4 g Novozym 525 (*Candida antarctica* B lipase, liquid preparation) to mixtures 3 and 4 and 0.4 g Novozym 388 (*Rhizomucor miehei* lipase, liquid preparation) to mixtures 5 and 6. The alcoholysis was carried out at room temperature on a multistirrer plate. Samples were taken after 16 hours and 44 hours and the content of glycerides was analyzed by gas chromatography. The results were evaluated as percentage areas.

| Mixture | Duration | % Ethyl ester | Monoglyceride content | Mono-:di-:triglyceride ratio |
|---|---|---|---|---|
| 1 | 16 | 0 | 0% | 0:12:88 |
| 1 | 44 | 0.7 | 0% | 0:4:96 |
| 2 | 16 | 55.1 | 26.5% | 63:33:4 |
| 2 | 44 | 61.1 | 23.3% | 69:31:0 |
| 3 | 16 | 0.7 | 0% | 0:2:98 |

-continued

| Mixture | Duration | % Ethyl ester | Monoglyceride content | Mono-:di-:triglyceride ratio |
|---|---|---|---|---|
| 3 | 44 | 2.2 | 0% | 0:4:96 |
| 4 | 16 | 0.7 | 0% | 0:2:98 |
| 4 | 44 | 2.2 | 0% | 0:4:96 |
| 5 | 16 | 7.6 | 0% | 0:4:96 |
| 5 | 44 | 4.9 | 1.2% | 2:7:91 |
| 6 | 16 | 2.1 | 0% | 0:3:97 |
| 6 | 44 | 4.1 | 0.9% | 1:5:94 |

Result:

Lipolase in the presence of a basic salt showed significant activity (mixture 2). If, by contrast, no salt was added, only a very weak alcoholysis reaction could be detected. Weak activity was detected with Novozym 388, but was not dependent on the addition of salt.

Example 3

Comparison of the Activity of Immobilized Lipolase and Lipolase Liquid Preparation Mixtures containing 0.2 g lipolase liquid preparation or a corresponding amount of lipolase fixed to a carrier were compared.

Immobilization of lipolase on Accurel® MP 1000 (Membrana): 5 g MP 1000 was placed in a 250 ml Erlenmeyer flask and 15 ml ethanol was added. The mixture was shaken for 1 hour, after which ethanol was decanted off. 50 g water was added to the MP 1000. After stirring for 1 hour, the water was decanted off. 100 ml phosphate buffer, 20 mM, pH 6.0, was added and the immobilization was started with the addition of 5 g lipolase liquid preparation. The mixtures were stirred overnight at 8° C., after which the enzyme immobilizate was filtered off. The immobilizate was dried overnight at room temperature between paper towels. The immobilizate was weighed out and a quantity of immobilizate corresponding to 0.2 g lipolase liquid preparation was used for the alcoholysis.

Immobilization of lipolase on Accurel MP 1000 (Membrana), alternative: Immobilization was carried out as described above. After the immobilizate had been filtered off, 5 ml of a 200 mM $Na_3PO_4$ solution was added. The complete mixture was dried in vacuo at room temperature. The object of this additional step was to prepare an already alkaline immobilizate. The immobilizate was weighed out and a quantity of immobilizate corresponding to 0.2 g lipolase liquid preparation was used for the alcoholysis.

Immobilization of lipolase on Dowex® Marathon WBA (Dow Chemical): 200 mg Dowex® WBA were placed in a small glass beaker. 0.2 g lipolase liquid preparation were added by pipette and thoroughly mixed with the tip of a pipette. The mixture was incubated for 2 hours at room temperature with occasional mixing. The complete mixture (Dowex resin+supernatant) was used for the transformation. Parallel tests where unbound lipolase was obtained from the immobilizate by washing out showed that around 90% of the lipolase present was fixed to a carrier.

Immobilization of lipolase on Duolite™ A 568 (Rohm & Haas): 200 mg Duolite A 568 were placed in a small glass beaker. 0.2 g lipolase liquid preparation were added by pipette and thoroughly mixed with the tip of a pipette. The mixture was incubated for 2 hours at room temperature with occasional mixing. The complete mixture (Duolite resin+supernatant) was used for the transformation. Parallel tests where unbound lipolase was obtained from the immobilizate by washing out showed that around 80% of the lipolase present was fixed to a carrier.

Test Procedure:

10 mixtures consisting of 40 g sunflower oil and 10 g ethanol were placed in glass beakers equipped with magnetic stirrers. 0.4 g water was added with stirring. 50 mg solid $Na_2CO_3$ were added to mixtures 2, 4, 6, 8 and 10. 0.2 g lipolase (*Thermomyces lanugenosus* lipase, liquid preparation) was added to mixtures 1 and 2, the Dowex resin immobilizates to mixtures 3 and 4, the Duolite resin immobilizates to mixtures 5 and 6, the MP 1000 immobilizates to mixtures 7 and 8 and the MP 1000 immobilizates aftertreated with $Na_3PO_4$ to mixtures 9 and 10. The alcoholysis was carried out at room temperature on a multistirrer plate. Mixtures 3 to 10 were treated twice. Samples were taken after 16 hours and the content of glycerides was analyzed by gas chromatography. The results were evaluated as percentages areas.

| Mixture | % Ethyl ester | Monoglyceride content | Mono-:di-:triglyceride ratio |
|---|---|---|---|
| 1 | 0 | 0% | 0:3:97 |
| 2 | 56.1 | 28.5% | 70:30:0 |
| 3 (1) | 25.6 | 11.5% | 16:23:61 |
| 3 (2) | 26.4 | 10.2% | 14:18:68 |
| 4 (1) | 31.6 | 14.1% | 21:36:44 |
| 4 (2) | 37.9 | 15.7% | 26:30:45 |
| 5 (1) | 17.6 | 7.4% | 9:13:78 |
| 5 (2) | 22.6 | 9.3% | 12:15:73 |
| 6 (1) | 35.5 | 17.1% | 27:34:39 |
| 6 (2) | 28.5 | 12.8% | 18:19:63 |
| 7 (1) | 15.5 | 5.5% | 7:20:73 |
| 7 (2) | 24.8 | 8.5% | 11:27:61 |
| 8 (1) | 26.1 | 10.5% | 14:37:49 |
| 8 (2) | 44.1 | 20.0% | 36:40:24 |
| 9 (1) | 24.4 | 9.1% | 12:43:45 |
| 9 (2) | 14.2 | 3.5% | 4:13:83 |

-continued

| Mixture | % Ethyl ester | Monoglyceride content | Mono-:di-:triglyceride ratio |
|---|---|---|---|
| 10 (1) | 8.4 | 2.4% | 3:18:79 |
| 10 (2) | 15.9 | 4.3% | 5:14:81 |

Result:

All the immobilizates containing lipolase showed alcoholysis activity. With the exception of the immobilizate pretreated with $Na_3PO_4$, all the immobilizates showed additional activation by $Na_2CO_3$. However, the activation of the liquid lipolase by $Na_2CO_3$ is considerably stronger than the activation of the immobilizates. For the same weighed quantity of enzyme, alcoholysis with salt-activated lipolase (mixture 2) was much faster than with the immobilizates. By contrast, immobilization allowed repeated use of the enzyme and hence the use of a larger quantity of enzyme.

Example 4

Reaction with Various Alcohols

Various mixtures consisting of 40 g sunflower oil and variable quantities of various alcohols were subjected to an alcoholysis reaction with lipolase at room temperature. The mixtures had the composition shown in the following Table:

| Mixture | Alcohol | Water | Salt | Lipolase |
|---|---|---|---|---|
| 1 | 10 g Ethanol | 0.4 g | 40 mg $Na_3PO_4$ | 0.4 g |
| 2 | 13 g Propanol | 0.4 g | 40 mg $Na_3PO_4$ | 0.4 g |
| 3 | 13 g Isopropanol | 0 g | 40 mg $Na_3PO_4$ | 1.2 g |
| 4 | 16 g Butanol | 0.4 g | 40 mg $Na_3PO_4$ | 0.4 g |
| 5 | 16 g Isobutanol | 0 g | 40 mg $Na_3PO_4$ | 1.2 g |
| 6 | 19 g Isoamyl alcohol | 0.4 g | 40 mg $Na_3PO_4$ | 0.8 g |
| 7 | 22 g Hexanol | 0.4 g | 40 mg $Na_3PO_4$ | 0.4 g |
| 8 | 28 g 2-Ethylhexanol | 0.4 g | 40 mg $Na_3PO_4$ | 1.2 g |
| 9 | 7 g Methanol | 0 g | 40 mg $Na_3PO_4$ | 1.2 g |
| 10 | 16 g Butanol | 0 g | 25 mg $Na_2CO_3$ | 1.2 g |
| 11 | 16 g Butanol | 0 g | 50 mg $Na_2CO_3$ | 0.6 g |
| 12 | 16 g Butanol | 0.8 g | 50 mg $Na_2CO_3$ | 0.6 g |
| 13 | 23 g Hexanol | 0.8 g | 25 mg $Na_2CO_3$ | 1.2 g |
| 14 | 24 g Hexanol | 2.8 g | 25 mg $Na_2CO_3$ | 1.2 g |
| 15 | 22 g Hexanol | 2.8 g | 50 mg $Na_2CO_3$ | 0.6 g |

The content of glycerides and esters was analyzed by gas chromatography. The results were evaluated as percentage areas, the excess free alcohols not being included. Samples were taken at the times shown in the Table.

| Mixture | Duration [h] | % Alkyl ester | Monoglyceride content | Mono-:di-:triglyceride ratio |
|---|---|---|---|---|
| 1 | 16 | 59.3 | 26.4% | 72:28:0 |
| 2 | 16 | 58.8 | 28.3% | 74:26:0 |
| 3 | 16 | 30.6 | 8.7% | 13:55:32 |
| 4 | 44 | 42.1 | 17.1% | 30:44:26 |
| 5 | 44 | 41.4 | 17.9% | 31:41:28 |
| 6 | 44 | 43.5 | 17.1% | 31:46:23 |
| 7 | 44 | 25.1 | 6.9% | 9:36:55 |
| 8 | 44 | 27.8 | 14.5% | 37:42:20 |
| 9 | 16 | 43.7 | 18.3% | 34:12:54 |
| 10 | 40 | 59.7 | 26.3% | 70:30:0 |
| 11 | 16 | 57.9 | 26.5% | 67:29:4 |
| 12 | 16 | 29.4 | 11.9% | 17:33:50 |
| 13 | 40 | 29.3 | 9.2% | 13:43:44 |
| 14 | 40 | 69.9 | 19.6% | 67:33:0 |
| 15 | 16 | 29.6 | 18.0% | 26:45:30 |

Result:

An alcoholysis reaction was observed with all the alcohols used. The enzyme accepts primary and secondary alcohols and linear and branched alcohols. The best reaction was observed with the alcohols ethanol and propanol in a reaction medium containing 2% water. For the other alcohols, the reaction conditions had to be slightly modified in part in order to achieve an optimal conversion. Detailed investigations with butanol (mixtures 10 to 12) and with hexanol (mixtures 13 to 15) showed that, even with these alcohols, the production of glycerides with a monoglyceride content of >60% is possible. The reaction with butanol takes place better in the medium containing relatively little water whereas the reaction with hexanol only takes place successfully in the presence of relatively large quantities of water. It may generally be concluded from this that the concentration of water has to be increased if the alcohol becomes more hydrophobic in order to achieve an optimal reaction rate.

Example 5

Influence of Ethanol Concentration on Glycerol Formation, Acid Formation and Monoglyceride Content Various mixtures consisting of 40 g sunflower oil with variable quantities of ethanol were subjected to an alcoholysis reaction with 0.2 g lipolase at room temperature. Quantities of 25 mg $Na_2CO_3$ were added. The mixtures had the composition shown in the following Table:

| Mixture | Ethanol | Water |
| --- | --- | --- |
| 1 | 15 g | 0.2 g |
| 2 | 30 g | 0.2 g |
| 3 | 15 g | 0.4 g |
| 4 | 30 g | 0.4 g |
| 5 | 15 g | 0.8 g |
| 6 | 30 g | 0.8 g |

The content of glycerides was analyzed by gas chromatography. The results were expressed as percentage areas. The glycerol content was also analyzed by gas chromatography. The results are expressed as non-calibrated percentage areas. According to a mass balance, the absolute glycerol contents are lower, although the key factor here is comparison of the relative values. GC samples were taken after a reaction time of 16 hours for the glycerol determination and after a reaction time of 40 hours for the glyceride determination. Acid values were determined after 16 hours.

Since glycerol shows a comparatively stronger adsorption than the ethyl esters and glycerides in the GC method used, a calibration was carried out directly in a mixture of ethyl ester, free ethanol and glycerides. The adsorption over a concentration range of 0 to 1.0% by weight glycerol corresponds to the formula:

$$y = 2.3x \text{ (y=adsorption, x=weighed amount)}$$

The following pattern emerges from the above analysis:

| Mixture | Glycerol measured | Glycerol (% by wt.) after calibration |
| --- | --- | --- |
| 1 | 1.5 | 0.65 |
| 2 | 0.3 | 0.13 |
| 3 | 2.4 | 1.04 |
| 4 | 0.5 | 0.22 |
| 5 | 2.8 | 1.22 |
| 6 | 1.1 | 0.48 |

Result:

The higher the concentration of alcohol used, the higher the monoglyceride contents obtained. Based on the total glycerides, monoglyceride contents of more than 90% can be achieved.

An increase in the alcohol content led to a reduction in the formation of by-products, such as free fatty acid or glycerol formed from the total hydrolysis of the oil.

The reaction rate was reduced when the alcohol content was increased, while the reaction rate was improved by increasing the water content. Good monoglyceride formation was achieved even with a large molar excess of ethanol (mixture 6).

Example 6

Reaction with Various Oils

Hydrolysis was investigated in parallel tests using various oils. 40 g of the oil was weighed into glass beakers with 10 g ethanol, then 0.4 g water was added with stirring, followed by the addition of 40 mg of solid $Na_3PO_4 \times 12H_2O$. The reaction was started by the addition of 0.4 g lipolase. After a reaction time of 16 hours, a sample was taken for analysis by gas chromatography, and the results are expressed as percentages areas.

| Mixture | Oil | % Ethyl ester | % Monoglyceride | Mono-:di-:triglyceride ratio |
| --- | --- | --- | --- | --- |
| 1 | Sunflower oil | 59.3 | 26.4% | 72:28:0 |
| 2 | Rapeseed oil | 58.7 | 26.4% | 73:27:0 |

| Mixture | Acid value | % Glycerol | % Ethyl ester | % Monoglyceride | Mono-:di-:triglyceride ratio |
| --- | --- | --- | --- | --- | --- |
| 1 | 2 | 1.5% | 62.2 | 29.2% | 86:14:0 |
| 2 | 1 | 0.3% | 34.5 | 11.4% | 18:35:47 |
| 3 | 3 | 2.4% | 64.3 | 26.2% | 86:14:0 |
| 4 | 1 | 0.5% | 58.9 | 30.6% | 77:23:0 |
| 5 | 5 | 2.8% | 64.7 | 25.8% | 87:13:0 |
| 6 | 2 | 1.1% | 62.4 | 32.2% | 92:8:0 |

-continued

| Mixture | Oil | % Ethyl ester | % Mono-glyceride | Mono-:di-:triglyceride ratio |
|---|---|---|---|---|
| 3 | Thistle oil | 60.9 | 26.0% | 76:24:0 |
| 4 | Sunflower oil 2 | 60.0 | 26.7% | 76:24:0 |
| 5 | Castor oil | 57.5 | 30.0% | 73:27:0 |
| 6 | Soybean oil | 60.3 | 26.4% | 75:25:0 |
| 7 | Fish oil | 51.0 | 35.0% | 78:22:0 |
| 8 | 50% rapeseed oil + 50% palm oil | 60.7 | 25.9% | 75:25:0 |
| 9 | Lard | 75.4 | 20.7% | 72:28:0 |

Result:

Good alcoholysis was observed with all the oils used. A monoglyceride content of >70%, based on total glycerides, was achieved with all the oils.

Example 7

Reaction with Various Alkaline Salts 5 mixtures of 40 g sunflower oil and 10 g ethanol were weighed in. 0.4 g water was added with stirring to all 5 mixtures. 40 mg $Na_3PO_4 \times 12H_2O$ was added to mixture 1; 11 mg $Na_2CO_3$ was added to mixture 2; 4 mg $Ca(OH)_2$ was added to mixture 3; 31 mg trisodium citrate×$2H_2O$ was added to mixture 4; and no salt was added to mixture 5. The reactions were started by the addition of 0.4 g lipolase. After a reaction time of 16 hours, a sample was taken for analysis by gas chromatography. The results are expressed as percentage areas.

| Mixture | % Ethyl ester | Monoglyceride content | Mono-:di-:triglyceride ratio |
|---|---|---|---|
| 1 | 59.3 | 26.4% | 72:28:0 |
| 2 | 62.1 | 23.3% | 74:26:0 |
| 3 | 50.5 | 28.9% | 65:35:0 |
| 4 | 1.0 | 0% | 0:3:97 |
| 5 | 0.7 | 0% | 0:2:98 |

Result:

The alcoholysis reaction was successful with the additions of phosphate salts, carbonate salts and hydroxides.

Example 8

Optimization of the Salt Concentration Used (for $Na_2CO_3$)

12 mixtures of 40 g sunflower oil and 10 g ethanol were weighed in. 0.2 g water was added with stirring to mixtures 1 to 6 and 0.4 g water was added to mixtures 7 to 12. Various quantities of salt as shown in the following Table were then added to the mixtures. The reactions were started by the addition of 0.2 g lipolase. After a reaction time of 16 hours, a sample was taken for analysis by gas chromatography. The results are expressed as percentage areas.

| Mixture | $Na_2CO_3$ | % Ethyl ester | Monoglyceride content | Mono-:di-:triglyceride ratio |
|---|---|---|---|---|
| 1 | 10 mg | 30.0 | 14.7% | 21:32 47 |
| 2 | 25 mg | 53.0 | 29.3% | 65:32:3 |
| 3 | 50 mg | 54.5 | 30.2% | 70:30:0 |
| 4 | 100 mg | 55.9 | 29.1% | 70:30:0 |
| 5 | 200 mg | 43.4 | 22.4% | 41:41:19 |
| 6 | 500 mg | 4.4 | 0.9% | 1:7:92 |
| 7 | 10 mg | 44.2 | 23.5% | 43:38:19 |
| 8 | 25 mg | 50.3 | 27.2% | 56:38:6 |
| 9 | 50 mg | 55.4 | 30.2% | 72:28:0 |
| 10 | 100 mg | 56.9 | 28.5% | 72:28:0 |
| 11 | 200 mg | 57.2 | 27.5% | 70:30:0 |
| 12 | 500 mg | 36.1 | 16.4% | 26:39:35 |

Result:

An increase in the water content in the mixture produces a slight shift in the optimal quantity of $Na_2CO_3$. With an addition of 0.2 g water, the range for the optimal quantity of salt extends from 25 mg to 100 mg whereas, with an addition of 0.4 g water, the optimal range is between 50 mg and 200 mg.

It should be noted that the optimum salt addition depends on the quantity of buffered enzyme solution used and on the strength of the salt. The test series with $Na_2CO_3$ may be regarded as exemplary.

Example 9

Influence of Temperature on the Transesterification Rate 6 mixtures of 40 g sunflower oil and 10 g ethanol were weighed in. 0.4 g water and 50 mg $Na_2CO_3$ were added to the mixtures with stirring. The reactions were started by the addition of 0.2 g lipolase. The reactions were carried out at different temperatures as shown in the following Table. After a reaction time of 24 hours, a sample was taken for analysis by gas chromatography. The results are expressed as percentage areas.

| Mixture | Temperature ° C. | % Ethyl ester | Monoglyceride content | Mono-:di-:triglyceride ratio |
|---|---|---|---|---|
| 1 | 20° C. | 30.0 | 14.7% | 21:32 47 |
| 2 | 25° C. | 53.0 | 29.3% | 65:32:3 |
| 3 | 30° C. | 54.5 | 30.2% | 70:30:0 |
| 4 | 35° C. | 55.9 | 29.1% | 70:30:0 |
| 5 | 40° C. | 43.4 | 22.4% | 41:41:19 |
| 6 | 45° C. | 4.4 | 0.9% | 1:7:92 |

Result:

The lipase is clearly deactivated even at temperatures as low as 30° C. upwards. The optimal reaction temperature is in the range from 20° to 25° C.

Example 10

Synthesis of Ethyl Ester/Partial Glyceride Mixtures with Measured Additions of Ethanol 1200 g rapeseed oil, 75 g ethanol, 0.375% water, based on the quantity of oil, and 0.025% NaOH with a concentration of 1 mol/l were introduced into a heatable 2-liter, double-jacketed reactor. The mixture was cooled with stirring to 15° C., after which 0.25% lipolase, based on the quantity of oil, was added. The mixture was incubated while stirring for 48 hours at 15° C. After 2.5 hours, another 75 g of ethanol was added and, after 5 hours, 150 g more of ethanol was introduced into the reactor. After 48 hours, the contents of the reactor were heated for 1 hour to 80° C. in order to deactivate the enzyme. The final product mixture was a single-phase mixture.

Analysis by gas chromatography produced the following composition (percentage areas, ethanol not included): 58.2% ethyl ester, 25.6% monoglyceride, 17.1% diglyceride, 0.7% triglyceride. Mathematically, the mixture still contains ca. 12% by weight free ethanol.

Example 11

Synthesis with Continuous Addition of Ethanol+Working Up of Ethyl Ester/Partial Glyceride Mixtures 1000 g rapeseed oil, 50 g ethanol and 0.025% NaOH with a concentration of 1 mol/l were introduced into a heatable 2-liter double-jacketed reactor. The mixture was cooled with stirring to 17° C., after which 0.25% lipolase, based on the quantity of oil, was added. The mixture was incubated while stirring for 45 hours at 17° C. After the reaction had been started, 200 g ethanol was pumped continuously into the reactor at a flow rate of 0.14 ml/min. After 45 more hours, 0.1% by weight Tonsil was introduced into the reactor and the contents of the reactor were heated. After incubation for 1 hour at 75° C., the contents of the reactor were filtered off. To remove residues of free glycerol, 500 g of the product was washed twice with 250 g water, the reaction system being stirred slowly in order to avoid emulsion formation. The glycerol- and alkali-containing aqueous phase was separated from the oil. The final product mixture was a clear, single-phase mixture.

Analysis by gas chromatography produced the following composition (percentage area, ethanol not included):

| A) Before removal of glycerol | B) After removal of glycerol |
|---|---|
| 56.9% ethyl ester | 59.9% ethyl ester |
| 28.6% monoglyceride | 29.6% monoglyceride |
| 14.2% diglyceride | 10.6% diglyceride |
| 0.3% triglyceride | 1.8% triglyceride |

Mathematically, the mixture still contains ca. 12% free ethanol before washing with water. The free glycerol content of the washed end product is below 0.05% by weight. Before washing, the product had a glycerol content after calibration of 1.1% by weight.

Example 12

Storage Stability of the Reaction Products of Example 11

The products of Example 11 were placed in glass bottles and stored for 55 days in daylight at room temperature. Comparative GC analyses were carried out.

| A) Before removal of glycerol | | B) After removal of glycerol | |
|---|---|---|---|
| Day 1 | Day 56 | Day 1 | Day 56 |
| 56.9% | 55.7% Ethyl ester | 59.9% | |
| 28.6% | 29.3% Monoglyceride | 29.6% | 28.6% Monoglyceride |
| 14.2% | 13.3% Diglyceride | 10.6% | 9.9% Diglyceride |
| 0.3% | 1.7% | 1.8% | 2.0% Triglyceride |

Result:

Within the accuracy limits of GC analysis, the samples were unchanged after 55 days. Accordingly, the biodiesel produced by the enzymatic process is stable in storage for at least 55 days.

Example 13

Removal of Glycerol from the Reaction Products of Example 11

50 g of the unwashed product of Example 11 was washed twice with 2% by weight water and twice with 5% by weight water. After each washing step, the aqueous phase was separated. The following glycerol contents were obtained:

| | Glycerol (% by weight) |
|---|---|
| Product before washing: | 1.1 |
| 2x washing with 50% water (Example 10) | <0.05 |
| 2x washing with 5% water | 0.15 |
| 2x washing with 2% water | 0.39 |

Result:

Glycerol can be removed from the product by washing with water over a broad concentration range and subsequent phase separation.

Example 14

Performance Tests in Diesel Fuels

Two samples of enzymatically-produced biofuel were tested as an additive to normal filling station diesel. The product of Example 10 was used for this purpose, both without removal of glycerol (code: USC-CM-8327-131DS) and after removal of glycerol by washing with water (code: USC-CM-8327-131).

USC-CM-8327-131:

Mixture of ethyl ester+monoglyceride+ethanol; glycerol content <0.05% by weight

USC-CM-8327-131 DS:

Mixture of ethyl ester+monoglyceride+ethanol; glycerol-containing (glycerol content >1% by weight)

The mixtures were tested for low-temperature behavior as 2.5, 3 and 5% by weight additions to filling station diesel. To this end, the CFPP values of the samples were determined.

| Biofuel [%] | USC-CM-8327-131 CFPP value [° C.] | USC-CM-8327-131 DS CFPP value [° C.] |
|---|---|---|
| 2.5 | −15 | −16 |
| 3 | −15 | −16 |
| 5 | −14 | −14 |

CFPP value, filling station diesel with no addition: −15° C.

Result:

In relatively low concentrations, there were no significant deteriorations in the CFPP. Only relatively high concentrations produced an increase in the CFPP by 1° C.

Storage of the two mixtures at low temperatures led to slight clouding in the diesel/biofuel mixture at −20° C. without any adverse effect on pumpability. At 4° C., the mixture remains unchanged, even after several weeks.

Example 15

Production of Monoglyceride-Containing Mixtures for Testing Lubricating Properties Mixture 1: 50 g Accurel MP 1000 was incubated for 1 hour with 500 g ethanol. After removal of the ethanol, 500 g water and 50 g lipolase were added and the mixture was stirred for 24 h. After removal of the water, the immobilizate was dried. The immobilizate was placed in a 3-liter reactor and 1.6 kg sunflower oil, 0.4 kg ethanol and 8 g water were added. The reaction mixture was incubated with stirring for 24 hours at room temperature. After the end of the reaction, the immobilizate was filtered off and the excess water/ethanol mixture was removed from the reactor. 16 g Tonsil and 2 g water were added to the sample, followed by incubation for 30 minutes at 80° C. The sample was then dried in vacuo and the Tonsil was removed by filtration. The ethyl ester/partial glyceride mixture thus obtained was used for the lubrication tests.

Mixture 2: 25 g lipolase was pipetted onto 25 g Dowex® Marathon WBA resin. The mixture was mixed and stored for 2 hours in a refrigerator for immobilization. 4 kg rapeseed oil and 1 kg ethanol were placed in a 6-liter reactor. The immobilizate was added to the reaction mixture with stirring, followed by incubation for 45 hours with stirring. After the reaction, the immobilizate was filtered off and the excess water/ethanol mixture was removed in a rotary evaporator at 80° C./50 mbar pressure. The ethyl ester/partial glyceride mixture was then subjected to short-path distillation. The ethyl esters were removed by distillation at 175° C. under a vacuum of 0.3 mbar. The bottom product was used for the lubrication tests.

Mixture 3: 25 g lipolase was pipetted onto 25 g Dowex Marathon WBA resin. The mixture was mixed and stored for 2 hours in a refrigerator for immobilization. 1.83 kg rapeseed oil and 0.7 kg butanol were placed in a 3-liter reactor. The immobilizate was added to the reaction mixture with stirring, followed by incubation for 60 hours with stirring. After the reaction, the immobilizate was filtered off and the excess water/butanol mixture was removed in a rotary evaporator at 80° C./50 mbar pressure. The butyl ester/partial glyceride mixture thus obtained was used for the lubrication tests.

The product compositions obtained are shown in Example 16.

Example 16

Testing of the Lubricating Properties in Diesel Fuel

The lubricating properties were subjected to an HFFR test (high-frequency reciprocating rig test) by Co-ordinating European Council CEC lubricity test method F-06-T-94. Various diesel fuels and monoglyceride mixtures based on sunflower oil and rapeseed oil from Example 15, as shown in the following Table, were used.

| Number | Sample | Raw material |
|---|---|---|
| Sample 1 | Monoglyceride/ethyl ester mixture | Sunflower oil |
| Sample 2 | Monoglyceride mixture distilled | Rapeseed oil |
| Sample 3 | Monoglyceride/butyl ester mixture | Rapeseed oil |

| | Ester | Monoglyceride | Diglyceride | Triglyceride |
|---|---|---|---|---|
| Sample 1 | 56.0 | 27.8 | 12.8 | <1 |
| Sample 2 | 3.5 | 61.0 | 32.0 | 2.5 |
| Sample 3 | 66.0 | 21.5 | 9.0 | <1 |

Results:

| Number | Concentration in diesel | HFFR value | Film |
|---|---|---|---|
| Diesel A | Blank | 411 µm | 19 µm |
| Sample 1 | 200 ppm | 261 µm | 67 µm |
| Diesel B | Blank | 542 µm | 20 µm |
| Sample 1 | 100 ppm | 311 µm | 65 µm |
| Sample 1 | 150 ppm | 217 µm | 70 µm |
| Sample 1 | 200 ppm | 231 µm | 68 µm |
| Diesel C | Blank | 615 µm | |
| Sample 2 | 100 ppm | 183 µm | |
| Sample 2 | 300 ppm | 170 µm | |
| Sample 3 | 100 ppm | 279 µm | |
| Sample 3 | 300 ppm | 195 µm | |

Result:

All samples significantly improve the lubricating properties of the diesel fuels used and reduce the HFFR values to below prescribed limits (for example, currently 450 µm in Switzerland).

Example 17

Enzymatic Synthesis of an Ethanol-containing Ethyl Ester/Partial Glyceride Mixture A total of 1600 kg refined rapeseed oil, 640 kg ethanol, 600 ml 1 M NaOH, 7 l water and 250,000 U lipase (esterase from *Thermomyces*, units according to the manufacturer) based on 1 kg rapeseed oil were placed in a 4000-liter reactor. The mixture was stirred for 40 hours, heated with stirring to 80° C. and then stirred for 2 hours at 80° C., the reactor remaining closed in order that no ethanol would escape. The mixture was then cooled to 50° C. and filtered through a drum filter containing 10 kg Celatom FW 14 (Eagle-Picher). The product was poured into casks and stored at room temperature.

Result:

2200 kg product were obtained, corresponding to a yield of 98%.

Example 18

Production of Distilled Ethyl Ester/Partial Glyceride Mixture 1600 kg refined rapeseed oil, 640 kg ethanol, 600 ml 1 M NaOH, 7 l water and 250,000 U lipase (esterase from *Ther-*

*momyces*, units according to the manufacturer), based on 1 kg rapeseed oil, were introduced into a 4000 l reactor. The mixture was stirred for 40 hours and then heated with stirring to 120° C. A vacuum was applied to the reactor and the ethanol/water mixture was removed from the reactor. The vacuum was slowly reduced until no more ethanol escaped from the mixture. The mixture was then cooled to 50° C. and filtered through a drum filter containing 10 kg Celatom FW 14. The product was poured into casks and stored at room temperature.

Result:

1742 kg product and 470 kg distillate were obtained, corresponding to a yield of 98%.

Example 19

Analysis of the Test Products from Examples 17 and 18

The analyses shown in the following Table were carried out with the test products of Examples 17 and 18.

| Values | Product of Example 17 | Product of Example 18 |
|---|---|---|
| Hydroxyl value | ca. 318-335 | 107 |
| Iodine value | 83 | 105 |
| Peroxide value | 9.1 | 9.6 |
| Acid value | 1.9 | 2.7 |
| Saponification value | 136 | 173 |
| Density | 0.875 g/ml | 0.9 g/ml |
| Color values | | |
| Lovibond 5¼ | 19/2.3 | 35/3.2 |
| Lovibond 1 | 2.0/0.6 | 3.5/0.8 |
| Gardner | 2.6 | 3.9 |
| Trace analysis | | |
| Nitrogen | <20 mg/kg | <20 mg/kg |
| Sulfur | <2 mg/kg | <2 mg/kg |
| Sodium | 8 mg/kg | 10 mg/kg |
| Iron | 0.4 mg/kg | 0.7 mg/kg |
| Phosphorus | <3 mg/kg | <3 mg/kg |
| Composition | | |
| Water content | 0.3 | 0.01 |
| Glycerol free | 0.20% | 0.30% |
| Glycerol bound | 6.80% | 9.00% |
| Ethanol | 21.90% | 0.20% |
| Ethyl ester | 41.00% | 55.50% |
| Monoglycerides | 23.00% | 32.20% |
| Diglycerides | 13.00% | 11.40% |
| Triglycerides | <1% | <1% |
| Fatty acid spectrum | | |
| Palmitic acid | 5.20% | 4.80% |
| Stearic acid | 1.30% | 1.30% |
| Oleic acid | 58.30% | 60.20% |
| Linoleic acid | 21.10% | 20.80% |
| Linolenic acid | 8.80% | 8.30% |

Result:

The test products are a mixture consisting mainly of ethyl esters and monoglycerides based on the fatty acid composition of rapeseed oil. Diglycerides are present in relatively small amounts; by-products are fatty acids and triglycerides. The non-distilled mixture additionally contains ethanol and a small amount of water. The test products have a good color corresponding to that of the oils used. The contents of organic and inorganic substances are low. Glycerol analysis shows that the glycerol of the triglyceride is almost completely bound in the form of the partial glycerides and less than 5% of the glycerol is present in free form.

Example 20

Stability of the Test Products of Examples 17 and 18

The products of Example 17 and Example 18 were placed in stoppered casks and stored for 3 months.

| | Product of Example 17 After synthesis | Product of Example 17 After 3 months | Product of Example 18 After synthesis | Product of Example 18 After 3 months |
|---|---|---|---|---|
| Composition | | | | |
| Ethyl ester | 41.00% | 40.10% | 55.50% | 55.00% |
| Monoglycerides | 23.00% | 22.30% | 32.20% | 31.20% |
| Diglycerides | 13.00% | 13.30% | 11.40% | 12.00% |
| Triglycerides | <1% | 1.90% | <1% | 0.90% |
| Glycerol free (titr.) | 0.20% | 0.25% | 0.30% | 0.50% |
| Glycerol free (GC) (not calibrated/area %) | 1.10% | 0.70% | 0.90% | 0.90% |
| Values | | | | |
| Acid value | 1.9 | 1.9 | 2.7 | 2.8 |
| POV | 9.1 | | 9.6 | |
| Lovibond | 2.0/0.6 | 1.9/0.6 | 3.5/0.8 | 3.0/0.8 |
| Gardner | 2.6 | 2.6 | 3.9 | 3.6 |

Result:

The products are sufficiently stable in storage for use as a diesel additive, wherein the product(s) is combined with the diesel fuel, or fuel additive for diesel, wherein the composition according to the invention may be combined with other additives before being added to the diesel fuel.

Example 21

Comparison of the Lubricating Effect Between FAME (Fatty Acid Methyl Ester) and the Composition According to the Invention The HFFR values of different mixtures of diesel with FAME were determined in comparison with a 3% mixture of the composition of Example 18 according to the invention and the lubricating effect of each thus investigated. The test is described in ISO 12156. In the test, a metal pin is drawn over a metal plate and the size of the scar is determined. It follows that the smaller the scar, the better is the lubricating effect.

The composition according to the invention which was added to diesel to obtain a 3% mixture contained the following % by weight distribution: 55.5% ethyl ester, 32.3% monoglycerides, 11.4% diglycerides, <1% by-products.

Results:

| HFFR Test to ISO 12156 | Wear scar [μm] |
|---|---|
| DIN EN 590 | 460 |
| Diesel | 600 |
| Diesel + 0.5% FAME | 540 |
| Diesel + 1% FAME | 370 |
| Diesel + 2.5% FAME | 320 |
| Diesel + 5% FAME | 310 |
| Diesel + 3% inventive composition | 220 |

It was shown that the addition of the composition according to the invention to conventional diesel improves lubricity disproportionally by comparison with mixtures with fatty acid methyl ester in various concentrations. The specific EN limit for the wear scar is 460 μm.

Example 22

Suitability of the Composition of Example 18 According to the Invention as a Fuel Additive Under EU Guidelines The improved lubricity of the composition of the instant invention is apparent and one of its distinct advantages.

Example 23

Chemical Partial Transesterification 93 g rapeseed oil, 4 g methanol and 3 g sodium methylate in methanol (20%) were introduced into a flask. The reaction mixture was heated with stirring and incubated while stirring for 1 hour under reflux through an attached reflux condenser. After the end of the reaction, the reaction mixture was neutralized with citric acid solution and washed with 50 g water. The product separated off was re-washed with 50 g water. The water phase was then removed. Samples were taken after the synthesis and after the two washing steps and analyzed by gas chromatography. The results are expressed as percentage areas. Small amounts of fatty acid formed are included in the ethyl ester area.

| Test | Saybolt Institute[1] Test method | ISO/ASTM equivalent Test method | Unit | 2.97% composition according to the invention Analysis results | Diesel Specification |
|---|---|---|---|---|---|
| | | | | Saybolt | EN 590 |
| Cetane number | EN ISO 5165 | ASTM D 613 | | 51.8 | min 51 |
| Cetane index | | ASTM D 976/ISO 4264 | | 49.7/50.3 | min 46 |
| Density at 15° C. | ASTM D 4052 | ISO 12185 | kg/l | 0.8341 | min 820/max 845 |
| Flash point | ASTM D 93 | ISO 2719 | ° C. | | min 55 |
| Flash point (PM) | | ISO 3679 | | 67 | |
| Viscosity at 40° C. | ASTM D 445 | ISO 3104 | mm/2 s | 2.453 | min 2.0/max 4.50 |
| Carbon Residue Method (on 10% dist res)[2] | ASTM D 4530 | ISO 10370 | wt % | <0.1 | max 0.30 |
| Cloud point | ASTM D 2500 | ISO 3015 | ° C. | −8 | only spec Arctic grades |
| Lubricity | ISO 12156 | ASTM D 6079 | μm | 220 | max 460 |
| Distillation (atmospheric) | ASTM D 86 | ISO 3405 | | | |
| Distillation (vacuum) | ASTM D 1160 | | | | |
| IBP[3] | | | ° C. | 175.1 | |
| 5% v | | | ° C. | 198.8 | |
| 10% v | | | ° C. | 207.2 | |
| 15% v | | | ° C. | 212.5 | |
| 20% v | | | ° C. | 217.7 | |
| 30% v | | | ° C. | 229.9 | |
| 40% v | | | ° C. | 242.2 | |
| 50% v | | | ° C. | 254.8 | |
| 60% v | | | ° C. | 268.5 | |
| 70% v | | | ° C. | 285.7 | |
| 78% v | | | ° C. | | |
| 80% | | | ° C. | 307.5 | |
| 90% v | | | ° C. | 333.3 | |
| 95% v | | | ° C. | 349.7 | max 360 |
| FBP[4] | | | ° C. | 354.9 | |
| % v recovered at 250° C. | | | % vol | 46.2 | max 65 |
| % v recovered at 350° C. | | | % vol | 95.3 | min 85 |

[1]Saybolt Institute: an independent testing institute in Rotterdam.
[2]Carbon residue method (on 10% dist res): this test is carried out to determine the carbon residues in the diesel. To this end, a sample is evaporated in a stream of nitrogen and the residue is weighed. For materials expected to produce a residue of less than 0.1%, a 10% distillation residue is first prepared and then measured. Determination of distillation behavior:
[3]IBP: initial boiling point
[4]FBP: final boiling point. The percentage figure represents the percentage of diesel evaporated at the respective temperatures

| Step | Glycerol | Ethyl ester | Monoglyceride | Diglyceride | Triglyceride |
|---|---|---|---|---|---|
| After Synthesis | 3.9% | 64.9% | 10.7% | 14.7% | 6.4% |
| Wash 1 | 1.6% | 64.4% | 10.9% | 15.5% | 7.6% |
| Wash 2 | 0.2% | 65.0% | 10.0% | 17.3% | 7.8% |

Result:

The chemical partial esterification gives a product mixture consisting of esters and partial glycerides from which large parts of glycerol can readily be removed simply by washing. The mixture obtained is a single-phase mixture. Of the total of 10% glycerol present in the triglyceride, less than 50% is released in the partial transesterification, the remaining glycerol being bound in the product. Accordingly, the stream of by-product glycerol is reduced by more than half in this process.

What is claimed is:

1. A composition comprising alkyl esters, monoglycerides and diglycerides which are present in the following quantities:

alkyl esters: 30 to 70%, by weight monoglyceride: 10 to 35%, by weight diglyceride: 1 to 30%, by weight the composition has a free glycerol content of <2% by weight, based on the total weight of the composition.

2. A composition according to claim 1, characterized in that it contains methyl esters, ethyl esters, or a mixture thereof as component (a).

3. A composition according to claim 1, characterized in that it has a partial glyceride content of at least 10%, by weight, based on the total weight of the composition.

4. A composition according to claim 1, characterized in that it has a triglyceride content of <5%, by weight, based on the total weight of the composition.

5. A composition according to claim 1, characterized in that it has an acid value of <5.

6. A composition according to claim 1, characterized in that the alkyl esters and partial glycerides are derived from saturated or unsaturated, linear or branched fatty acids containing 8 to 22 carbon atoms.

* * * * *